(12) United States Patent
Maji et al.

(10) Patent No.: US 9,402,059 B2
(45) Date of Patent: Jul. 26, 2016

(54) MICROSCOPE

(71) Applicant: SHIMADZU CORPORATION, Kyoto (JP)

(72) Inventors: Takeshi Maji, Kyoto (JP); Tomoki Sasayama, Kyoto (JP); Kazumi Yokota, Osaka (JP)

(73) Assignee: SHIMADZU CORPORATION, Kyoto (JP)

( * ) Notice: Subject to any disclaimer, the term of this patent is extended or adjusted under 35 U.S.C. 154(b) by 702 days.

(21) Appl. No.: 13/727,621

(22) Filed: Dec. 27, 2012

(65) Prior Publication Data
US 2013/0242078 A1  Sep. 19, 2013

(30) Foreign Application Priority Data
Mar. 13, 2012 (JP) ................. 2012-055972

(51) Int. Cl.
H04N 7/18 (2006.01)
G02B 21/08 (2006.01)
G02B 21/24 (2006.01)
G02B 21/36 (2006.01)
G01N 21/35 (2014.01)
G02B 21/16 (2006.01)

(52) U.S. Cl.
CPC .............. H04N 7/18 (2013.01); G01N 21/35 (2013.01); G02B 21/088 (2013.01); G02B 21/244 (2013.01); G02B 21/361 (2013.01); G02B 21/16 (2013.01)

(58) Field of Classification Search
CPC .......... H04N 7/18; G02B 21/088; G01N 21/35
USPC .................. 348/79, 61, 86, 95, 117, 129, 142
See application file for complete search history.

(56) References Cited

U.S. PATENT DOCUMENTS

| | | | |
|---|---|---|---|
| 2009/0103173 A1* | 4/2009 | Akao et al. | 359/368 |
| 2009/0231422 A1* | 9/2009 | Fukuyama | G02B 21/24 348/79 |
| 2011/0255745 A1* | 10/2011 | Hodder et al. | 382/103 |
| 2012/0044340 A1* | 2/2012 | Yamamoto | 348/79 |

FOREIGN PATENT DOCUMENTS

JP  2000-121554  4/2000

* cited by examiner

Primary Examiner — Thai Tran
Assistant Examiner — Nien-Ru Yang
(74) Attorney, Agent, or Firm — Jianq Chyun IP Office

(57) ABSTRACT

A microscope is provided. The microscope includes: a detection section for detecting the measurement light; a first image acquisition section emitting the visible light onto a detection surface to obtain an optical image; and a switch mirror or beam splitter disposed on a light path, along which the measurement light from the analysis position of the sample is guided to the detection section. The microscope further includes a second image acquisition section that is disposed in a position apart from the light path of the detection section for obtaining an optical image of a large area which includes the analysis position of the sample, wherein the optical image of the large area is larger than an optical image of an area, which includes the analysis position of the sample, obtained by the first image acquisition section.

11 Claims, 7 Drawing Sheets

MICROSCOPE

CROSS-REFERENCE TO RELATED APPLICATION

This application claims the priority benefit of Japan application serial no. 2012-055972, filed on Mar. 13, 2012. The entirety of each of the above-mentioned patent application is hereby incorporated by reference herein and made a part of this specification.

BACKGROUND OF THE INVENTION

1. Field of the Invention

The invention relates to a microscope which emits a light for measurement, e.g. infrared light, ultraviolet light, visible light, etc., to a microscopic analysis position of a surface of a macroscopic sample.

2. Description of Related Art

An infrared microscope is used for examining a molecular structure based on a functional group of an organic compound attached to a solid surface (of a sample), for example. Specifically, an infrared light, which is condensed to a small diameter, is emitted to a particular microscopic part (e.g. an analysis position of 15 µm×15 µm) of the sample surface. Because the microscopic part of the sample surface generates a particular spectrum of the molecular structure based on the functional group of the organic compound, the spectrum is detected and analyzed for identification and quantification of the organic compound (see Patent Reference 1, for example).

The aforementioned infrared microscope includes an image acquisition section, e.g. CCD camera, CMOS camera, etc., for the analyst to observe the sample surface. By using the image acquisition section, an optical image of the sample surface can be observed to determine the analysis position of the sample surface. For example, a light source, e.g. a halogen lamp, is used to emit a visible light to an position of the sample surface that includes the analysis position and a visible light reflected from the area including the analysis position is detected by the CCD camera to form the optical image, which is shown as an optical image picture, for the analyst to observe and designate where the infrared light is to be emitted on the sample and where an analysis range is on the sample.

FIG. 6 is a structural diagram illustrating main components of a conventional infrared microscope, wherein a direction that is level with the ground is defined as an X direction, a direction perpendicular to the X direction that is level with the ground is defined as a Y direction, and a direction perpendicular to the X direction and the Y direction is defined as a Z direction. An infrared microscope 101 includes a sample stage 10 (sample disposing mechanism) carrying a sample S, an infrared light source section 20 for emitting an infrared light, a visible light source section 30 for emitting a visible light, a detection section 240 for detecting the infrared light, an image acquisition section 50 having a detection surface for detecting the visible light, Cassegrain lenses 260 and 261 (optical elements), a plate-shaped exchange lens 70, and a computer 190 for controlling the whole infrared microscope 101.

The sample stage 10 includes a micro-movement stage (sample platen) which is movable, an X direction driving mechanism (not shown), a Y direction driving mechanism (not shown), and a Z direction driving mechanism (not shown). The sample S may be disposed on or removed from the top of the micro-movement stage. A sample stage controlling section 191a of the computer 190 outputs a necessary driving signal to the aforementioned driving mechanisms to move the micro-movement stage to the X direction, Y direction, and Z direction as desired.

The infrared light source section 20 is a Fourier transform infrared spectrophotometer for emitting the infrared light having an intensity that varies with time (interferogram). In addition, the infrared light source section 20 is disposed in a way that the emitted infrared light is condensed by the Cassegrain lenses 260 and 261 and emitted to the analysis position (e.g. 15 µm×15 µm) of the sample S on the sample stage 10 after being reflected by a mirror 21, an exchange mirror 22, a penetration/reflection exchange mirror 23, concave lenses 24 and 25, and translucent lenses 26 and 27. The detection section 240 includes a detector 241, a condenser lens 242, and a mirror 243. The condenser lens 242 and the mirror 243 are disposed before the detector 241.

The visible light source section 30 is used to emit the visible light. Moreover, the visible light source section 30 is disposed in a way that the emitted visible light is condensed by the Cassegrain lenses 260 and 261 and emitted to the area that includes the analysis position of the surface of the sample S carried on the sample stage 10 after penetrating through and being reflected by a lens 31, the exchange mirror 22, the penetration/reflection exchange mirror 23, the concave lenses 24 and 25, and the translucent lenses 26 and 27. The image acquisition section 50 includes a CCD camera 51 having the detection surface for detecting the visible light and a relay lens 52 disposed before the CCD camera 51.

In order for the image acquisition section 50 to acquire the optical image of the area that includes the analysis position of the surface of the sample S by the same optical axis (light path) that an optical system guides the infrared light to the detection section 240, an exchange lens 270 is disposed on the light path (in a −Z direction) above the sample stage 10, along which the infrared light is guided to the detection section 240, and the exchange lens 270 may be moved to a position that intersects the light path or be moved away from the light path. Accordingly, the infrared light from the analysis position of the sample S is condensed by the Cassegrain lens 260 and transmitted in the predetermined direction (−Z direction), and after being reflected to a −X direction by the exchange lens 270 on the light path, the infrared light is detected by the detection section 240. Additionally, the visible light from the area that includes the analysis position of the surface of the sample S is condensed by the Cassegrain lens 260 and transmitted in the predetermined direction (−Z direction) to be detected by the detection surface of the CCD camera 51.

The computer 190 includes a CPU 191 (control section) and is connected with a monitor 93 (display device) and an operation section 92 (input device). Referring to the block diagram that illustrates the functions performed by the CPU 191, the CPU 191 includes a sample stage control section 191a for controlling the sample stage 10, an image acquisition control section 191b for acquiring the optical image from the image acquisition section 50 and displaying the optical image picture (measurement picture) on the monitor 93, and an analysis control section 191c for performing a Fourier transform and calculating an infrared spectrum by obtaining infrared light information of the analysis position of the sample S from the detection section 240.

FIG. 7 illustrates an example of the picture displayed by the monitor of the infrared microscope 101. The measurement picture (e.g. 500 µm×400 µm) obtained from the image acquisition section 50 is displayed by the monitor 93. A dotted-line quadrilateral analysis position picture is shown in the measurement picture to indicate the analysis position (e.g. 50 µm×50 µm) in the current position relationship of the micro-movement stage.

The sample stage control section 191a is used for controlling the micro-movement stage to move in the X direction, the Y direction, and the Z direction according to a signal from the operation section 92. For instance, the analyst observes the measurement picture displayed by the monitor 93 and at the same time uses the operation section 92 to perform operations, such as dragging by mouse or scroll bar, on the measurement picture, so as to designate the position (analysis position) of the sample S, to which the infrared light is emitted. Accordingly, the sample stage control section 191a moves the micro-movement stage in the X direction, the Y direction, and the Z direction, such that the infrared light is emitted to the designated position. In addition, if the position is not desirable, the analyst may repeat the operation to correct the position, check the position of the analysis position picture on the measurement picture, and then begin the measurement. In other words, the analyst produces a picture of the area including the analysis position of the surface of the sample S by the CCD camera 51 and determines the desired analysis position based on the measurement picture. Alternatively, the analyst may visually inspect at which side of the sample S the optical axis of the measurement optical system is located to approximately align the position. Furthermore, if the position is not desirable, the analyst repeats the operation to correct the position by visual inspection, check the position of the analysis position picture on the measurement picture, and then begin the measurement.

RELATED ART

Patent Reference

[Patent Reference 1] JP 2000-121554

SUMMARY OF THE INVENTION

Problem to be Solved by the Invention

Nevertheless, because of the Cassegrain lens 260, a magnification of the optical image obtained by the image acquisition section 50 of the aforementioned infrared microscope 101 is high (15-30 times, for example). As a result, the analyst cannot see the entirety of the surface of the sample S, and when the analyst designates the position that is to be irradiated by the infrared light, the analyst needs to move the micro-movement stage slightly each time and use the operation section 92 to vary the range of the surface of the sample S displayed on the measurement picture, which is time-consuming. Moreover, it has been considered to prepare an additional optical element for observing the entirety of the surface of the sample S as the measurement picture and to switch to the additional optical element as necessary. However, the following problem is raised accordingly: a low magnification is limited to about 5, and switching for the additional optical element takes time and may cause a displacement, etc. Accordingly, the invention provides a microscope for easily designating the position of the sample to be irradiated by a measurement light, such as infrared light, ultraviolet light, and visible light, etc., in a short period of time.

Solution to the Problem

In view of the aforementioned problems, the invention provides a microscope which includes a measurement light source section for emitting a measurement light to an analysis position of a sample, a visible light source section for emitting a visible light to an area including the analysis position of the sample, a detection section for detecting the measurement light from the analysis position of the sample, a first image acquisition section for emitting the visible light from the area including the analysis position of the sample onto a detection surface to obtain an optical image, and a beam dividing means disposed on a light path that guides the measurement light from the analysis position of the sample to the detection section and guiding the visible light from the area including the analysis position of the sample to the detection surface of the first image acquisition section by switching or splitting the light path, wherein the sample is moved with respect to the detection section and the first image acquisition section. The microscope further includes a second image acquisition section disposed in a position apart from the light path that leads to the detection section and obtaining an optical image of a large area including the analysis position of the surface of the sample by guiding the visible light to the detection section, wherein the optical image of the large area is larger than an optical image of the area including the analysis position of the surface of the sample obtained by the first image acquisition section.

Here, the measurement light is an infrared light, an ultraviolet light, and a visible light, etc., for example. Moreover, with an interferometer or other modulating means, an intensity of the measurement light may vary with time. In addition, the beam dividing means can be any device that spatially and spectrally divides a light beam and introduces the same to two detectors (the detection section and the first image acquisition section). For example, the beam dividing means may be a switch lens and a beam splitter, etc. Furthermore, the beam splitter may be an element, such as a dichroic mirror, for dividing spectral penetration and reflection or an element, such as an edge mirror or a polkadot mirror, for dividing spatial penetration and reflection.

Effect of the Invention

As described above, in addition to the conventional first image acquisition section, the microscope of the invention further includes at least one second image acquisition section that has a light path independent from the first image acquisition section. The second image acquisition section is mainly used for obtaining an image of the whole sample. According to the above, because the optical image of the large area including the analysis position of the surface of the sample obtained by the second image acquisition section is larger than the optical image obtained by the first image acquisition section, the analyst can view the optical image of the large area from the top and easily designate the position irradiated by the measurement light in a short period of time without repeating the operation.

Solution to Other Problems and Effect Thereof

In addition, the second image acquisition section of the microscope of the invention may further include a zoom in/out mechanism for zooming in or zooming out the obtained optical image of the large area. When using the microscope of the invention, the optical image of the large area can be zoomed in or zoomed out to a size that facilitates observation of the surface of the sample. Accordingly, approximate position alignment becomes easier.

In addition, according to the microscope of the invention, the second image acquisition section obtains the visible light by an optical axis different from an optical axis of an optical system that guides the measurement light to the detection section, and the microscope further comprises a control section, correcting a distortion of the optical image of the large area obtained by the second image acquisition section such that the optical image of the large area is obtained by a same optical axis as the optical system that guides the measurement light to the detection section, and displaying a picture of the optical image of the large area. According to the microscope of the invention, if the optical axis of the optical system of the second image acquisition section has an angle with respect to the optical axis of the optical system of the first image acquisition section, the optical image of the large area is obtained by observing the sample from an inclined angle and thus the optical image is distorted. Moreover, the second image acquisition section and the first image acquisition section generally have different distortions. Thus, by correcting the distortion of the optical image of the large area obtained by the second image acquisition section, the optical image of the large area is obtained by a same optical axis as the optical system that guides the measurement light to the detection section, the position irradiated by the measurement light can be accurately designated. In addition, by correcting the distortion between the second image acquisition section and the first image acquisition section, the images obtained by the second image acquisition section and the first image acquisition section can correspond to each other and be handled directly, and determination of the position becomes easy.

Furthermore, the microscope of the invention may further include a sample disposing mechanism for moving the sample stage that carries the sample. Additionally, the control section in the microscope of the invention may display a picture of the optical image obtained by the first image acquisition section and a picture of the optical image of the large area at the same time or in turn. Moreover, the control section in the microscope of the invention may display at least one of an optical image position picture, which indicates a position of the picture of the optical image obtained by the first image acquisition section, and an analysis position picture, which indicates the analysis position, on the picture of the optical image of the large area.

Further to the above, the control section in the microscope of the invention may move the sample stage according to an operation performed on the position of the optical image position picture or the analysis position picture on the picture of the optical image of the large area via an input device. For example, an exclusive operation section, such as a joy stick or a keyboard, may be disposed separately for the microscope of the invention for controlling the movement of the sample stage. The sample stage is configured to move together with operations, such as dragging the optical image position picture or the analysis position picture on the picture of the optical image of the large area or double-clicking on the picture of the optical image of the large area to notify a desired position, for the analyst to designate the position more intuitively and directly. Accordingly, the operation for the determination of position becomes easier and the time required is shortened.

In addition, according to the microscope of the invention, when the sample stage moves in a direction of the light path that leads to the detection section, a direction of a view center of the second image acquisition section may be varied, such that a view center of the first image acquisition section and the view center of the second image acquisition section on the surface of the sample are consistent to each other. According to the microscope of the invention, if the optical axis of the optical system of the second image acquisition section has an angle with respect to the optical axis of the optical system of the first image acquisition section, a center position (view center) of each optical axis on the sample becomes inconsistent with each other when the sample stage moves in the direction of the light path that leads to the detection section. In that case, the direction of the view center of the second image acquisition section is varied according to the movement of the sample stage in the direction of the light path that leads to the detection section. Since the misalignments of the observation position and the focusing state are corrected, the analysis position can be accurately determined regardless of the movement of the sample stage in the direction of the light path that leads to the detection section. The above is also applicable to a situation when a thick sample is disposed on the sample stage or an auxiliary sample holding mechanism is disposed on the sample stage.

Furthermore, the microscope of the invention further includes an optical element for condensing the measurement light from the measurement light source section and emitting the condensed measurement light to the analysis position of the sample and condensing a light from the area including the analysis position of the sample and emitting the condensed light, wherein the optical element is a Cassegrain lens having a Cassegrain main lens and a Cassegrain auxiliary lens, and an optical system for guiding light to the second image acquisition section or the detection surface of the second image acquisition section may be disposed on a back side of the Cassegrain auxiliary lens. According to the microscope of the invention, the light of the central section on the back side of the Cassegrain auxiliary lens is not used. Thus, the light for the measurement optical system is not obstructed by the second image acquisition section and optical system disposed on the back side of the Cassegrain auxiliary lens.

Additionally, in the microscope of the invention, the second image acquisition section obtains the visible light by the same optical axis as the optical system that guides the measurement light to the detection section, and the control section may include a control section that displays the optical image of the large area obtained by the second image acquisition section as the picture of the optical image of the large area. Because the second image acquisition section of the microscope of the invention acquires the visible light by the same optical axis as the optical system that guides the measurement light to the detection section, the position irradiated by the measurement light can be accurately designated.

Moreover, according to the microscope of the invention, a focusing range of the first image acquisition section and a focusing range of the second image acquisition section may overlap each other. According to the microscope of the invention, a magnification of the second image acquisition section is lower than a magnification of the first image acquisition, and therefore, a focal depth of the second image acquisition section is deeper than a focal depth of the first image acquisition. For this reason, when the sample that has an uneven surface is moved on a horizontal plane, the analysis position may be out of focus and cannot be captured by the first image acquisition section. However, with the second image acquisition section, the problem that the sample may be out of focus is improved and the time required for determining the position is reduced.

DESCRIPTION OF THE EMBODIMENTS

The following paragraphs explain embodiments of the invention with reference to the figures. Nevertheless, the invention is not restricted to the embodiments disclosed below, and various modifications may be made to the disclosure without departing from the spirit and scope of the invention.

First Embodiment

Figure 1:
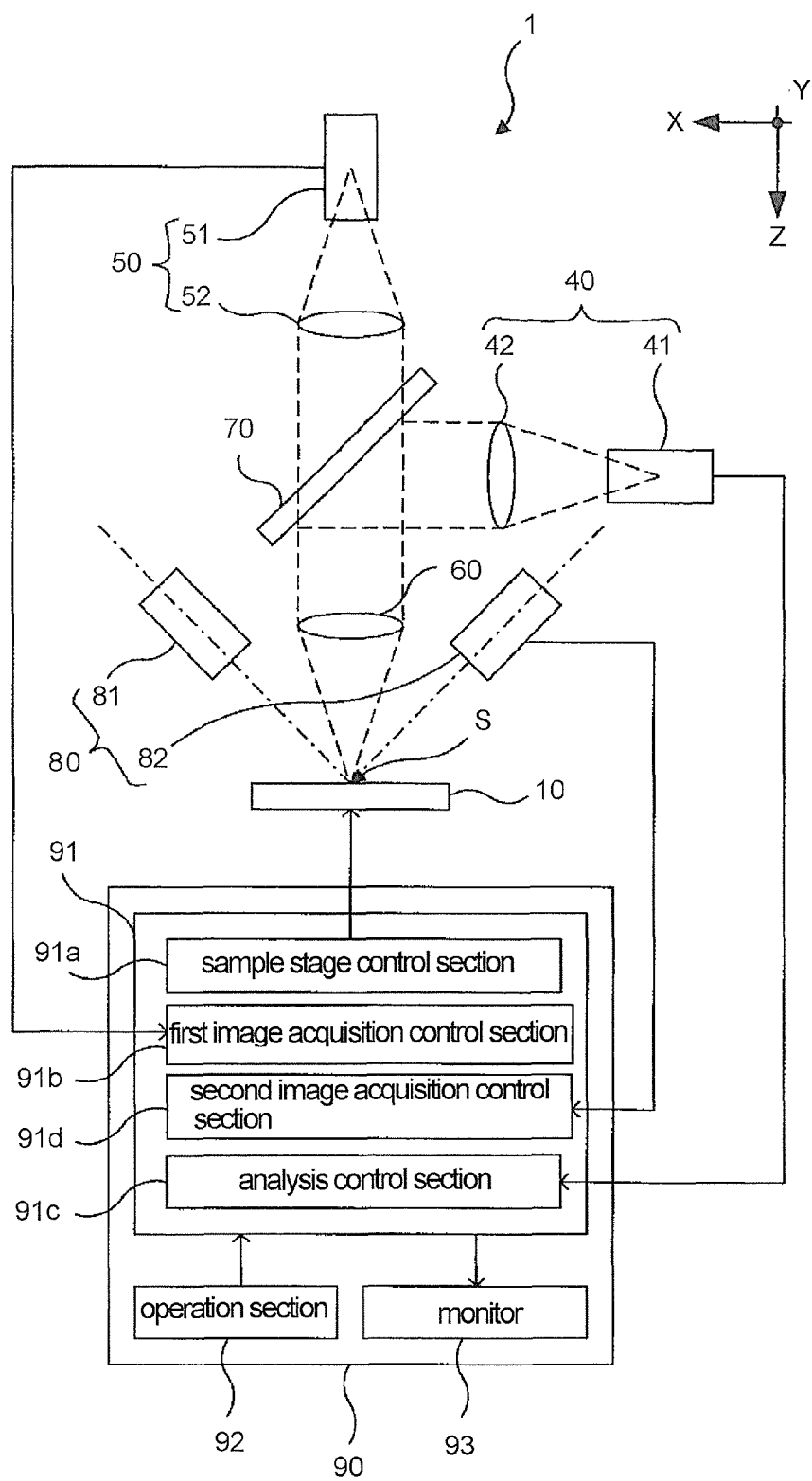
FIG. 1 is a structural diagram illustrating main components of a microscope according to the first embodiment.

FIG. 1 is a structural diagram illustrating main components of a microscope according to the first embodiment. FIG. 1 illustrates a sample and components between a detector and a camera section used for acquiring an observed image. Optical systems for introducing a visible light and a measurement light are omitted from FIG. 1. A microscope 1 includes a sample stage 10 for carrying a sample S, a measurement light source section (not shown) for emitting the measurement light, a visible light source section (not shown) for emitting the visible light, a detection section 40 for detecting the measurement light, a first image acquisition section 50 having a detection surface for detecting the visible light, a second image acquisition section 80 having a detection surface for detecting the visible light, an optical element 60, a plate-shaped beam splitter 70, and a computer 90 for controlling the whole microscope 1.

The second image acquisition section 80 includes a CCD camera 81 having a detection surface for detecting the visible light, a CCD camera 82 having a detection surface for detecting the visible light, and movement mechanisms (not shown) for moving the CCD cameras 81 and 82. The CCD camera 81 is disposed in an upper-left direction (having a predetermined angle (45°) with respect to an optical axis of an optical system (optical element 60, etc.) that guides the measurement light to the detection section 40) of the sample stage 10 and the detection surface thereof faces toward a lower-right direction. The CCD camera 82 is disposed in an upper-right direction (having a predetermined angle (−45°) with respect to the optical axis of the optical system (optical element 60, etc.) that guides the measurement light to the detection section 40) of the sample stage 10 and the detection surface thereof faces toward a lower-left direction.

When the aforementioned second image acquisition section 80 is used, the visible light from a large area (an entirety of a surface of the sample S) that includes an analysis position of the surface of the sample S is detected by the detection surfaces of the CCD camera 81 and the CCD camera 82. In other words, the visible light is detected by the detection surfaces of the CCD camera 81 and the CCD camera 82 without passing through the optical element 60. In addition, the magnifications of the CCD camera 81 and the CCD camera 82 are respectively lower than a magnification of the first image acquisition section 50, and thus the focal depths of the CCD camera 81 and the CCD camera 82 are deeper than a focal depth of the first image acquisition section 50. When the sample S, which has an uneven surface, is moved on a horizontal plane (an XY plane), a portion of the object under measurement may be out of focus and cannot be captured by the first image acquisition section 50. With the CCD camera 81 and the CCD camera 82, the problem that the sample S may move out of focus is improved and the time required for determining the positions is reduced. In addition, focusing positions of the two (more than one) cameras, i.e. CCD camera 81 and CCD camera 82, are set to be different at a depth direction of the sample S. With respect to a sample having multiple focusing positions, the focal depth needs to be deeper. By using two or more cameras, when the CCD camera 81 and the CCD camera 82 are used to obtain the image of the sample S, only the portions that are in focus are taken and combined. Thus, an image with the whole sample S in focus can be obtained without impairing the brightness of the view, and an additional focusing operation can be omitted to shorten the time for determining the position.

Figure 2:
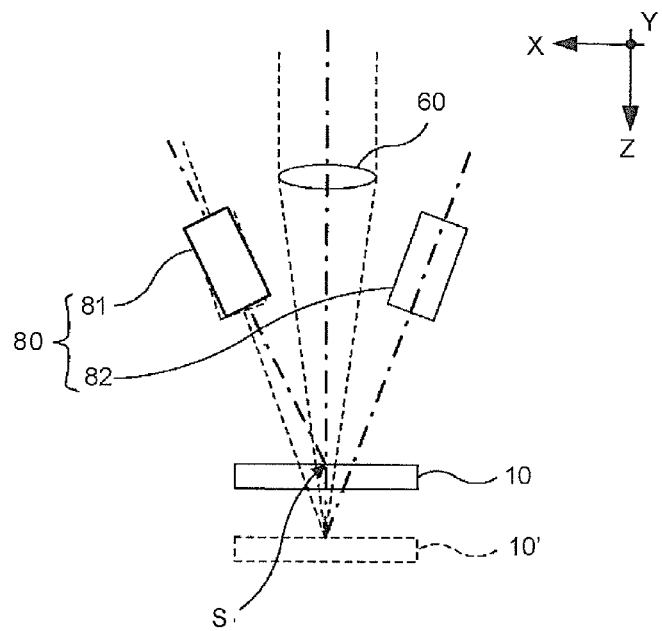
FIG. 2 is a diagram illustrating a movement of a CCD camera.

Moreover, the CCD camera 81 may be rotated by the movement mechanism with the Y direction as a rotation axis for changing a direction of a view center thereof corresponding to a movement of the micro-movement stage to the Z direction. The CCD camera 82 may also be rotated by the movement mechanism with the Y direction as the rotation axis for changing a direction of a view center thereof corresponding to the movement of the micro-movement stage to the Z direction. FIG. 2 is a diagram illustrating movements of the CCD cameras 81 and 82. In the second image acquisition section 80, a top surface of the micro-movement stage is located in the focusing position of the optical system of the first image acquisition section 50, and rotation angles of the CCD cameras 81 and 82 are adjusted such that an optical axis center of the optical system of the first image acquisition section 50 is consistent with the optical axis centers of the CCD cameras 81 and 82, and the angles are recorded in advance. The angles are adjusted during fabrication. If the micro-movement stage is moved to the Z direction, the CCD cameras 81 and 82 are rotated corresponding to the movement of the micro-movement stage to maintain the optical axis center of the optical system of the first image acquisition section 50 consistent with the view centers of the CCD cameras 81 and 82. Moreover, if the sample S is very thick or the thickness of an auxiliary sample disposing and holding mechanism causes a problem, the micro-movement stage is moved in the Z direction to a position that is approximately in focus of a CCD camera 51 and the CCD cameras 81 and 82. Then, the position is detected to determine a difference between the position and the original focusing position (when the aforementioned thicknesses are not taken into consideration) on the Z axis, and the CCD cameras 81 and 82 are further rotated according to the difference to maintain the optical axis center of the optical system of the first image acquisition section 50 consistent with the view centers of the CCD cameras 81 and 82. Thus, even if the micro-movement stage is moved to a position 10', the visible light from the large area (the entirety of the surface of the sample S) that includes the analysis position of the surface of the sample S can still be detected by the detection surfaces of the CCD camera 81 and the CCD camera 82. In addition, the optical systems of the CCD cameras 81 and 82 can focus on the focusing position of the optical system (optical element 60) that guides the measurement light to the detection section 40. That is, misalignment of the observation position and the focusing state can be corrected.

The computer 90 includes a CPU 91 (control section) and is connected with a monitor 93 (display device) and an operation section 92 (input device). Referring to the block diagram that illustrates the functions performed by the CPU 91, the CPU 91 includes a sample stage control section 91a for controlling the sample stage 10, a first image acquisition control section 91b for acquiring an optical image (measurement picture) from the first image acquisition section 50 and displaying the same on the monitor 93, a second image acquisition control section 91d for acquiring an optical image from the second image acquisition section 80 and displaying the same on the monitor 93, and an analysis control section 91c for performing a Fourier transform and calculating a spectrum by obtaining measurement light information of the analysis position of the sample S from the detection section 40.

The second image acquisition control section 91d controls the acquisition of the optical image from the second image acquisition section 80 and the display of the optical image on the monitor 93. The second image acquisition control section 91d corrects a distortion of the optical image of the large area (the entirety of the surface of the sample S) such that the optical image of the large area is obtained from the second image acquisition section 80 by using a same optical axis as the optical system (optical element 60, etc.) that guides the measurement light to the detection section 40, and displays a picture (top-view picture) of the optical image of the large area. Here, the correction is carried out, for example, by using the CCD cameras 81 and 82 to capture images of a grid sample in advance and recording positions of grid points in the CCD cameras 81 and 82 to determine inclinations of the optical systems of the CCD cameras 81 and 82, and performing picture compensation and correction by transforming the captured picture according to the foregoing information.

Figure 3:
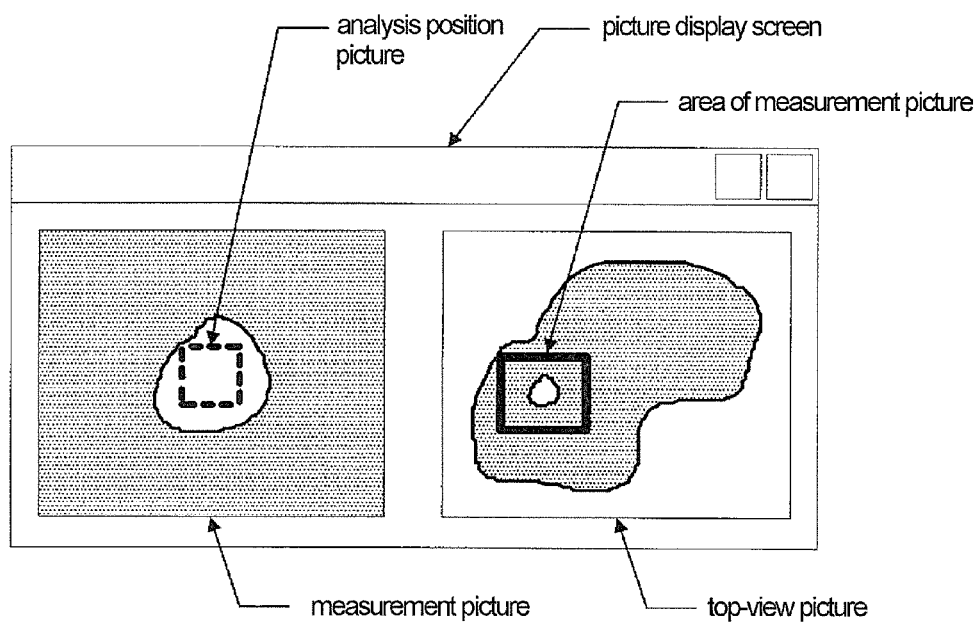
FIG. 3 illustrates an example of the picture displayed by a monitor of the microscope according to the first embodiment.

FIG. 3 illustrates an example of the picture displayed by the monitor of the microscope 1. A measurement picture (e.g. 500 μm×400 μm) obtained from the first image acquisition section 50 in the current position relationship of the micro-movement stage is shown in a left area of the monitor 93, and the picture of the optical image of the large area (e.g. 10,000 μm×10,000 μm) obtained from the second image acquisition section 80 is shown in a right area of the monitor 93. A dotted-line quadrilateral analysis position picture is depicted in the measurement picture to indicate the analysis position (e.g. 50 μm×50 μm) in the current position relationship of the micro-movement stage. Moreover, a solid-line quadrilateral measurement picture position picture is depicted in the picture of the optical image of the large area to indicate the position of the measurement picture.

The dotted-line quadrilateral corresponds to the analysis position and varies with a sample mask area and a sample aperture size of the device. In addition, if the optical element 60 is changed to vary the magnification, a measurement picture corresponding to the magnification is displayed and a size of the dotted-line quadrilateral is also changed correspondingly to the magnification. On the other hand, the solid-line quadrilateral indicates a range displayed by the measurement picture and varies with the magnification of the optical element 60. In other words, the solid-line quadrilateral varies corresponding to the size of the actual measurement picture area. Here, although not shown in the figure, an analysis position picture which denotes the analysis position (e.g. 50 μm×50 μm) may also be displayed on the picture of the optical image of the large area. The aforementioned quadrilaterals may be located in any position of the picture and is not restricted to a central portion of the picture. Moreover, in FIG. 3, the measurement picture and the picture of the optical image of the large area are displayed simultaneously. However, these pictures may be selectively switched and displayed. Additionally, in the case that multiple CCD cameras are disposed, the picture of the optical image of the large area may be displayed once while it is also fine that more than one particular picture may be selectively switched and displays. Furthermore, each picture may be dynamically displayed as a pop-up window according to the requirements.

In addition, a movement operation is performed to the measurement picture, the picture of the optical image of the large area, the dotted-line quadrilateral, and the solid-line quadrilateral displayed by the second image acquisition control section 91d. And, the sample stage control section 91a controls the sample stage 10 to move corresponding to the movement operation. For example, when the solid-line quadrilateral is dragged and dropped by a mouse, information of the movement of the solid-line quadrilateral (e.g. the number of pixels of the picture and a cursor movement of the mouse, or a movement of the stage and a stage position designation amount corresponding to these above movements, etc.) is transmitted to the sample stage control section 91a for the sample stage control section 91a to perform position change promptly. Accordingly, a state and a picture after the position is changed are reflected on a picture display screen. If required, the movement is sent to the sample stage control section 91a while the solid-line quadrilateral is being dragged, so as to continuously update the position of the sample stage 10 and the picture.

When using the microscope 1, the analyst first designates an area of the sample S that includes a predetermined position, which is to be irradiated by the measurement light, by using the operation section 92 to perform operations, such as dragging by mouse or scroll bar, on the picture of the optical image of the large area while observing the picture of the optical image of the large area displayed by the monitor 93. Accordingly, the sample stage control section 91a moves the sample stage 10 in the X direction, the Y direction, and the Z direction, so as to display the designated position as the measurement picture. Next, the analyst designates a position (analysis position) of the sample S that is irradiated by the measurement light by using the operation section 92 to perform operations, such as dragging by mouse or scroll bar, on the measurement picture while observing the measurement picture displayed by the monitor 93. Thereby, the sample stage control section 91a moves the sample stage 10 in the X direction, the Y direction, and the Z direction to match the designated position with the position irradiated by the measurement light. Then, the analyst confirms the position of the picture of the analysis position on the measurement picture and begins the measurement.

As disclosed above, the microscope 1 of the invention includes the second image acquisition section 80 that obtains the optical image (top-view picture) of the large area including the analysis position of the surface of the sample S, and the obtained optical image of the large area is larger than the optical image obtained by the first image acquisition section 50. Therefore, the analyst can intuitively and directly perform designation without paying special attention to the switch between designation of the approximate position on the picture of the optical image of the large area and designation of the precise position on the measurement picture. In addition, the distortion of the optical image of the large area obtained by the second image acquisition section 80 is corrected such that the optical image of the large area is obtained via the same optical axis as the optical system that guides the measurement light to the detection section 40, and thus the position irradiated by the measurement light can be accurately designated.

Second Embodiment

Figure 4:
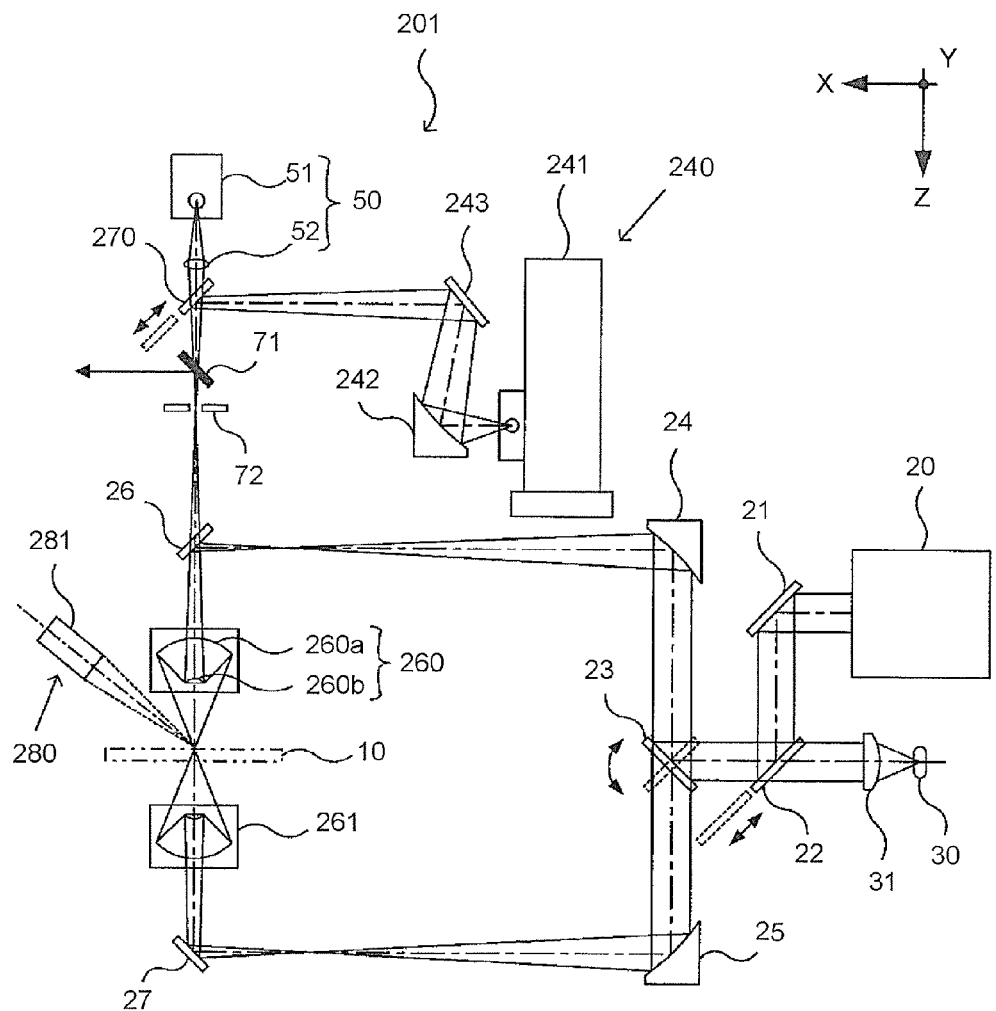
FIG. 4 is a structural diagram illustrating main components of an infrared microscope according to the second embodiment.

FIG. 4 is a structural diagram illustrating main components of an infrared microscope according to the second embodiment. In addition, elements identical to those of the infrared microscope 101 are denoted by the same reference numerals. An infrared microscope 201 includes the sample stage 10 for carrying the sample S, the infrared light source section 20 for emitting the infrared light, the visible light source section 30 for emitting the visible light, the detection section 240 for detecting the infrared light, the first image acquisition section 50 having the detection surface for detecting the visible light, a second image acquisition section 280 having a detection surface for detecting the visible light, the Cassegrain lenses 260 and 261 (optical elements), the plate-shaped exchange lens 270, and a computer (not shown) for controlling the whole infrared microscope 201.

The Cassegrain lens 260 (Schwarzschild reflective objective lens) includes a Cassegrain main lens 260a and a Cassegrain auxiliary lens 260b. The Cassegrain auxiliary lens 260b has a round shape when viewed from the Z direction. From the Y direction and the X direction, the Cassegrain auxiliary lens 260b has a convex top surface with a hemispherical shape and a planar bottom surface. Moreover, the Cassegrain auxiliary lens 260b is disposed above the sample stage 10, and the top surface of the Cassegrain auxiliary lens 260b faces upward (−Z direction). Furthermore, the Cassegrain main lens 260a is in a circular shape with an opening that has the same shape as the Cassegrain auxiliary lens 260b when viewed from the Z direction. From the Y direction and the X direction, the Cassegrain main lens 260a has a concave bottom surface with a hemispherical shape and a planar top surface. In addition, the Cassegrain main lens 260a is disposed above the sample stage 10 and the Cassegrain auxiliary lens 260b and the top surface of the Cassegrain main lens 260a faces upward (−Z direction). Accordingly, the infrared light from the infrared light source section 20 is reflected by the Cassegrain auxiliary lens 260b and then condensed by the Cassegrain main lens 260a to irradiate the analysis position of the sample S. Moreover, the light from the area that includes the analysis position of the sample S is condensed by the Cassegrain main lens 260a and then reflected to the −Z direction by the Cassegrain auxiliary lens 260b. The Cassegrain lens 261 (Schwarzschild reflective objective lens) has the same structure as the Cassegrain lens 260. The Cassegrain lenses 260 and 261 are symmetrically disposed on two opposite sides of the sample stage 10.

The second image acquisition section 280 includes a CCD camera 281 that has the detection surface for detecting the visible light. The CCD camera 281 is disposed in an upper-left direction (having a predetermined angle (45°) with respect to an optical axis of an optical system (Cassegrain lens 260, etc.) that guides the infrared light to the detection section 40) of the sample stage 10 and the detection surface thereof faces toward a lower-right direction. When the second image acquisition section 280 is used, the visible light from the large area (the entirety of the surface of the sample S) that includes the analysis position of the sample S is detected via the detection surface of the CCD camera 281. In other words, the visible light is detected by the detection surface of the CCD camera 281 without passing through the Cassegrain lens 260.

As disclosed above, the infrared microscope 201 of the invention can be used to obtain the optical image (top-view picture) of the large area that includes the analysis position on the surface of the sample S, and the optical image of the large area is larger than the optical image obtained by the first image acquisition section 50. Therefore, the analyst can easily designate the position irradiated by the infrared light when observing the picture of the optical image of the large area and the measurement picture.

Third Embodiment

Figure 5:
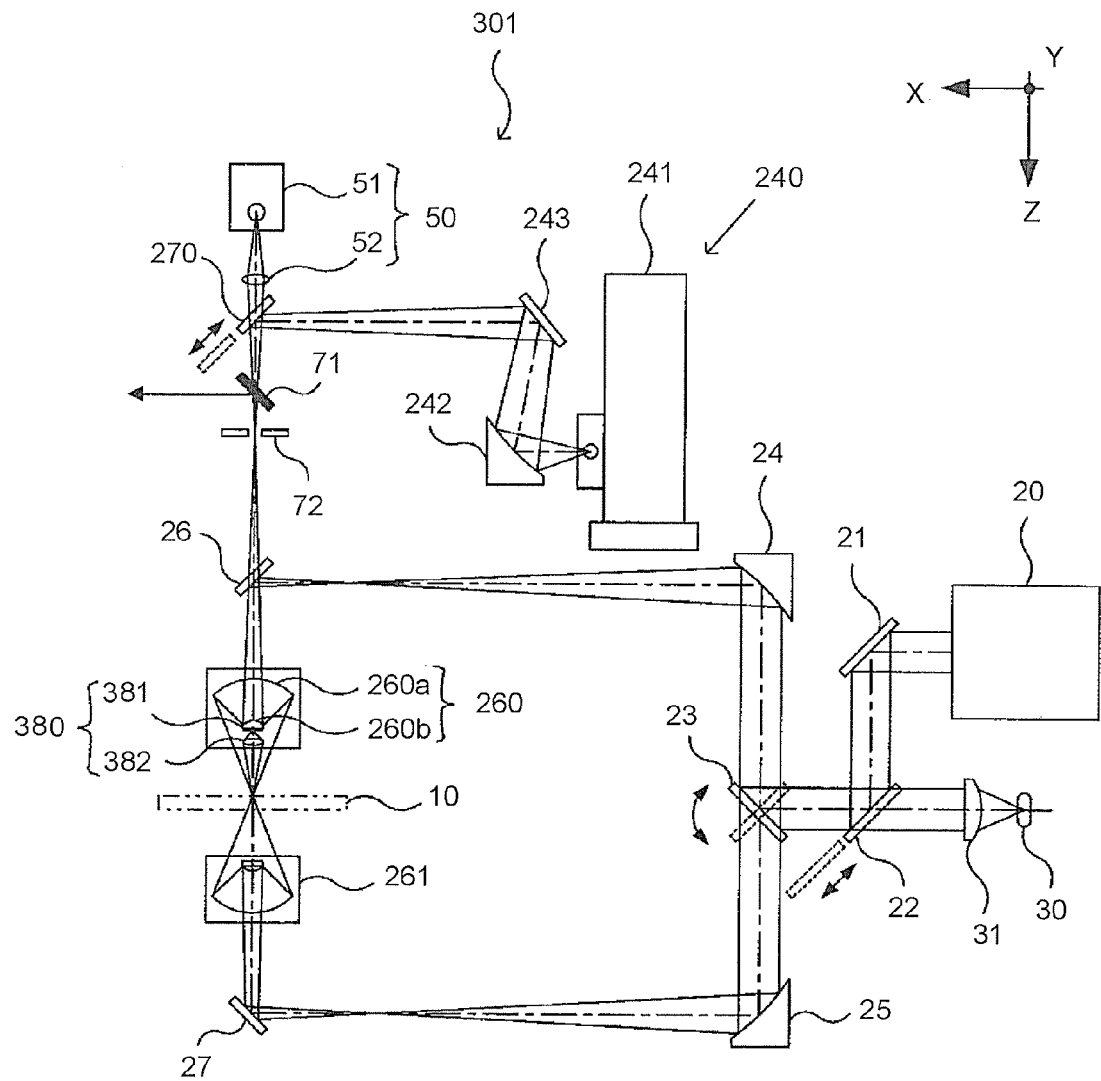
FIG. 5 is a structural diagram illustrating main components of an infrared microscope according to the third embodiment.
Figure 6:
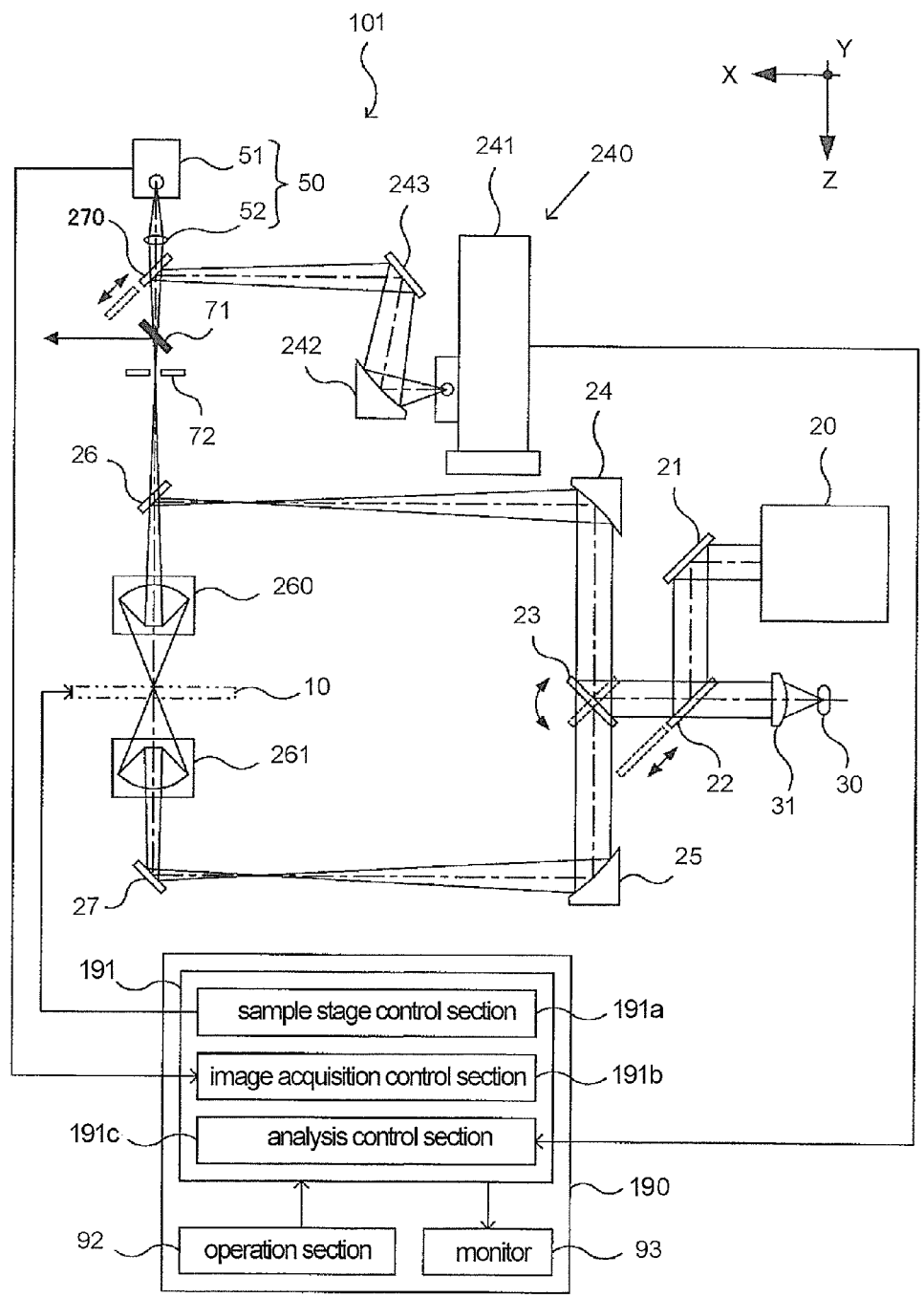
FIG. 6 is a structural diagram illustrating main components of a conventional infrared microscope.
Figure 7:
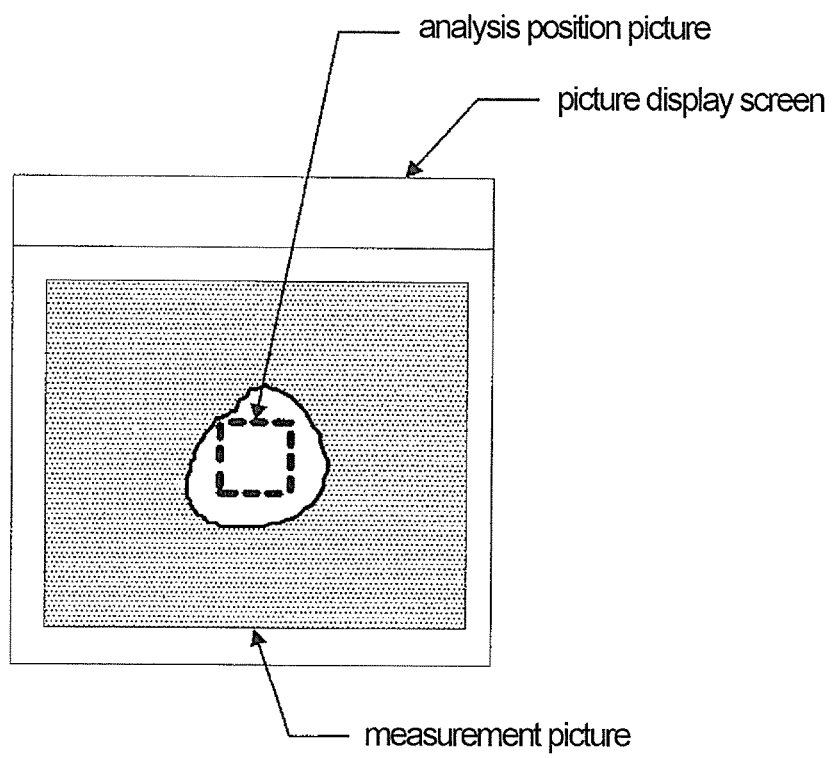
FIG. 7 illustrates an example of the picture displayed by a monitor of the conventional infrared microscope.

FIG. 5 is a structural diagram illustrating main components of an infrared microscope according to the third embodiment. In addition, elements identical to those of the infrared microscope 101 are denoted by the same reference numerals. An infrared microscope 301 includes the sample stage 10 for carrying the sample S, the infrared light source section 20 for emitting the infrared light, the visible light source section 30 for emitting the visible light, the detection section 240 for detecting the infrared light, the first image acquisition section 50 having the detection surface for detecting the visible light, a second image acquisition section 380 having a detection surface for detecting the visible light, the Cassegrain lenses 260 and 261 (optical elements), the plate-shaped exchange lens 270, and a computer (not shown) for controlling the whole infrared microscope 301.

The second image acquisition section 380 includes a CCD camera 381 having the detection surface for detecting the visible light and a photographing lens 382 disposed in front of the CCD camera 381. The CCD camera 381 is disposed above the sample stage 10 (in a position having the same optical axis as the Cassegrain lens 260, etc.) and below the Cassegrain auxiliary lens 260b (back side), and the detection surface of the CCD camera 381 faces downward. When the aforementioned second image acquisition section 380 is used, the visible light from the large area (the entirety of the surface of the sample S) that includes the analysis position of the sample S is detected by the detection surface of the CCD camera 381 via the photographing lens 382. That is, the visible light is detected by the detection surface of the CCD camera 381 without passing through the Cassegrain lens 260.

As described above, the infrared microscope 301 of the invention can be used to obtain the optical image (top-view picture) of the large area that includes the analysis position of the sample S, and the optical image of the large area is larger than the optical image obtained by the first image acquisition section 50. Therefore, the analyst can easily designate the position irradiated by the infrared light when observing the picture of the optical image of the large area and the measurement picture. Additionally, the optical systems of the first image acquisition section 50 and the second image acquisition section 280 in the infrared microscope 201 cannot have the same optical axis. Thus, the optical axis of the optical system of the second image acquisition section 280 is inclined and causes the problem of picture distortion (especially for an infrared microscope having the Schwarzschild reflective objective lens, the problem of picture distortion is more obvious because the Cassegrain lens 260 has a greater radius and correspondingly the angle of the optical axis of the optical system of the second image acquisition section 280 becomes greater with respect to the optical axis of the optical system of the first image acquisition section 50). By contrast, the second image acquisition section 380 obtains the visible light by the same optical axis as the optical system (Cassegrain lens 260, etc.) that guides the infrared light to the detection section 240, and the control section displays the optical image of the large area obtained by the second image acquisition section 380 as the picture of the optical image of the large area (top-view picture). Therefore, the position irradiated by the infrared light can be accurately designated.

Other Embodiments (1) In the above-described microscope 1, the first image acquisition section 50 is disposed above the beam splitter 70 and the detection section 40 is disposed on the right side of the beam splitter 70. Nevertheless, the microscope 1 may have a structure with the first image acquisition section 50 disposed on the right side of the beam splitter 70 and the detection section 40 disposed above the beam splitter 70.

(2) In the above-described microscope 1, the CCD cameras 81 and 82 may have a structure that includes a zoom in/out mechanism capable of zooming in and zooming out the obtained optical image of the large area. The zoom in/out mechanism is achieved for example by using an optical means, e.g. using a zoom lens, or a digital means, e.g. cropping a part of the image captured by a high-pixel image capture element.

Figure 8:
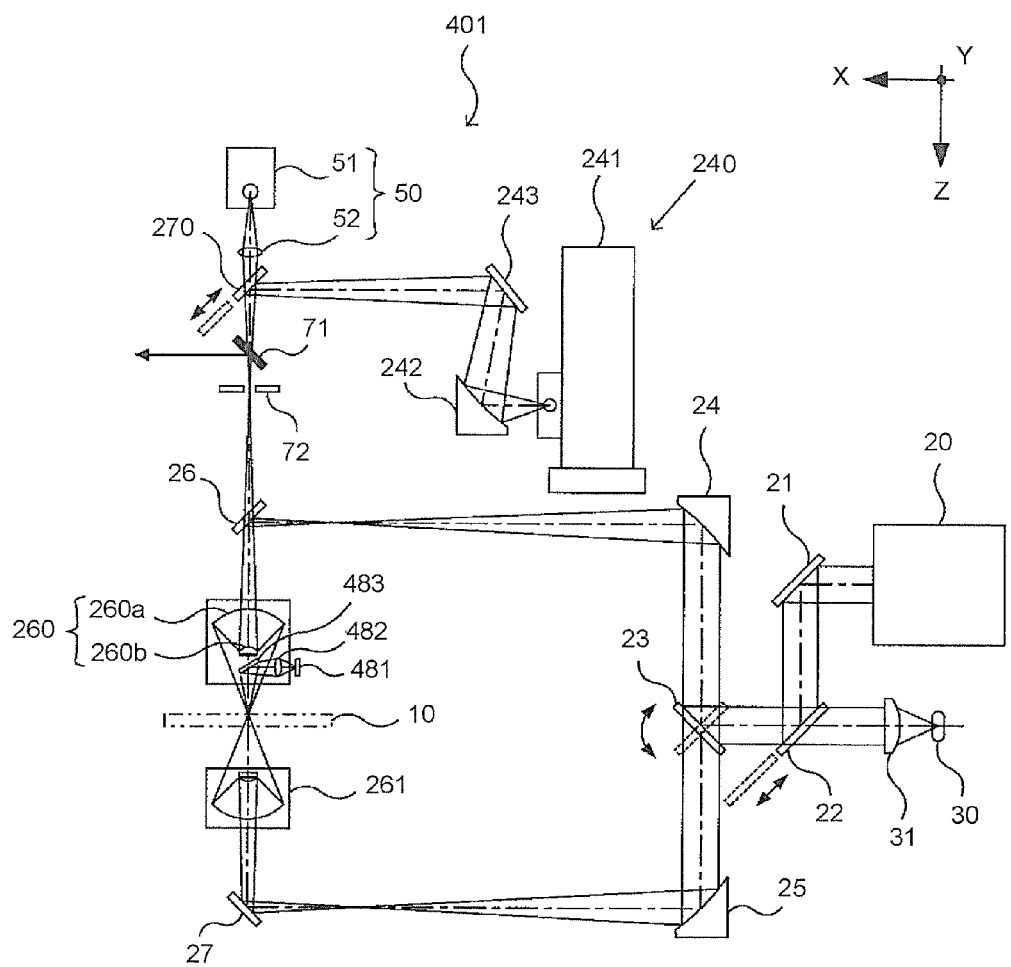
FIG. 8 is a structural diagram illustrating main components of an infrared microscope according to the fourth embodiment.

(3) In the above-described microscope 1, the second image acquisition section 80 includes two cameras, i.e. CCD cameras 81 and 82. However, the second image acquisition section 80 may include three or more than three cameras. (4) In the above-described infrared microscope 301, the CCD camera 381 and the photographing lens 382 are disposed below the Cassegrain auxiliary lens 260b (back side). However, a CCD camera 481 and a photographing lens 482 may be disposed in a position (right side, for example) not below the Cassegrain auxiliary lens 260b (back side), and in that case, a mirror 483 is disposed below the Cassegrain auxiliary lens 260b (back side) for guiding light to the CCD camera 481 and the photographing lens 482 (on the right side, for example). FIG. 8 is a structural diagram illustrating main components of an infrared microscope 401 according to the fourth embodiment. In addition, elements identical to those of the infrared microscope 301 are denoted by the same reference numerals.

INDUSTRIAL APPLICABILITY

The invention is adapted for a microscope, etc., that irradiates a sample with a measurement light and detects a spectrum emitted by the sample accordingly.

What is claimed is:

1. A microscope, comprising:
a measurement light source section emitting a measurement light to an analysis position of a sample;
a visible light source section emitting a visible light to an area comprising the analysis position of the sample;
a detection section detecting the measurement light from the analysis position of the sample;
a first image acquisition section receiving the visible light from the area comprising the analysis position of the sample onto a detection surface to obtain an optical image; and
a beam splitter disposed on a light path that guides the measurement light from the analysis position of the sample to the detection section and guiding the visible light from the area comprising the analysis position of the sample to the detection surface of the first image acquisition section by switching or splitting the light path,
wherein the sample is moved with respect to the detection section and the first image acquisition section, and
the microscope further comprises a second image acquisition section disposed in a position apart from the light path that leads to the detection section and obtaining an optical image of a large area comprising the analysis position of the sample simultaneously as the first image acquisition section obtains the optical image by guiding the visible light to the detection section, wherein the optical image of the large area obtained by the second image acquisition section is larger than an optical image of the area comprising the analysis position of the sample obtained by the first image acquisition section.

2. The microscope according to claim 1, wherein the second image acquisition section further comprises a zoom in/out mechanism zooming in or zooming out the obtained optical image of the large area.

3. The microscope according to claim 1, wherein the second image acquisition section obtains the visible light by an optical axis different from an optical axis of an optical system that guides the measurement light to the detection section, and
the microscope further comprises a control section, correcting a distortion of the optical image of the large area obtained by the second image acquisition section such that the optical image of the large area is obtained by using an optical axis the same as the optical axis of the optical system that guides the measurement light to the detection section, and displaying a picture of the optical image of the large area.

4. The microscope according to claim 1, further comprising a sample disposing mechanism for moving a sample stage that carries the sample.

5. The microscope according to claim 4, wherein the control section displays a picture of the optical image obtained by the first image acquisition section and a picture of the optical image of the large area at the same time or in turn.

6. The microscope according to claim 5, wherein the control section displays at least an optical image position picture, which indicates a position of the picture of the optical image obtained by the first image acquisition section, and an analysis position picture, which indicates the analysis position, on the picture of the optical image of the large area.

7. The microscope according to claim 6, wherein the control section moves the sample stage according to an operation performed on the position of the optical image position picture or the analysis position picture on the picture of the optical image of the large area via an input device.

8. The microscope according to claim 6, wherein when the sample stage moves in a direction of the light path that leads to the detection section, a direction of a view center of the second image acquisition section is varied, such that a view center of the first image acquisition section and the view center of the second image acquisition section on a surface of the sample are consistent to each other.

9. The microscope according to claim 1, further comprising an optical element condensing the measurement light from the measurement light source section and emitting the condensed measurement light to the analysis position of the sample and condensing a light from the area comprising the analysis position of the sample and emitting the condensed light, wherein the optical element is a Cassegrain lens comprising a Cassegrain main lens and a Cassegrain auxiliary lens, and an optical system for guiding light to the second image acquisition section or the detection surface of the second image acquisition section is disposed on a back side of the Cassegrain auxiliary lens.

10. The microscope according to claim 9, wherein the second image acquisition section obtains the visible light by a same optical axis as the optical system that guides the measurement light to the detection section, and the control section is a control section displaying the optical image of the large area obtained by the second image acquisition section as a picture of the optical image of the large area.

11. The microscope according to claim 9, wherein a focusing range of the first image acquisition section and a focusing range of the second image acquisition section overlap each other.

* * * * *